United States Patent [19]

Knowles et al.

[11] Patent Number: 5,393,670
[45] Date of Patent: Feb. 28, 1995

[54] **DNA, VECTORS AND TRANSFORMED HOSTS ENCODING *TRICHODERMA REESEI* ENDOGLUCANASE I**

[75] Inventors: Jonathan Knowles, Geneva, Switzerland; Merja Penttilä, Helsinki; Tuula Teeri, Espoo, both of Finland; Helena M. K. Nevalainen, North Epping, Australia; Päivi Lehtovaara-Helenius, Helsinki, Finland

[73] Assignee: Oy Alko AB, Helsinki, Finland

[21] Appl. No.: 95,253

[22] Filed: Jul. 23, 1993

Related U.S. Application Data

[60] Continuation of Ser. No. 418,154, Oct. 6, 1989, which is a division of Ser. No. 817,942, Jan. 30, 1986, Pat. No. 4,894,338.

[30] Foreign Application Priority Data

Apr. 13, 1984 [FI] Finland .................................. 841500

[51] Int. Cl.$^6$ ....................... C12N 1/21; C12N 15/52; C12N 15/70; C12N 15/81
[52] U.S. Cl. ........................ 435/252.33; 435/69.8; 435/172.3; 435/209; 435/254.11; 435/254.2; 435/254.21; 435/945; 536/23.2; 536/23.74
[58] Field of Search .................... 435/69.1, 69.7, 69.8, 435/172.3, 320.1, 209, 252.3, 252.33, 254.11, 254.2, 254.21, 945; 536/23.2, 23.4, 23.74

[56] References Cited

U.S. PATENT DOCUMENTS

| | | | |
|---|---|---|---|
| 4,165,974 | 10/1986 | Kingsman et al. | 435/69.1 |
| 4,338,397 | 7/1982 | Gilbert et al. | 435/69.1 |
| 4,394,443 | 7/1983 | Weissman et al. | 435/6 |
| 4,794,125 | 12/1988 | Nunberg et al. | 536/24.3 |

FOREIGN PATENT DOCUMENTS

| | | | |
|---|---|---|---|
| 32530/84 | 3/1985 | Australia | C12N 15/00 |
| 0011767 | 6/1980 | European Pat. Off. | C12N 9/42 |
| 0073635 | 3/1983 | European Pat. Off. | C12N 15/00 |
| 0088632 | 9/1983 | European Pat. Off. | C12N 15/00 |
| 0137280 | 4/1985 | European Pat. Off. | C12N 15/00 |
| WO84/00175 | 1/1984 | WIPO | C12N 15/00 |

OTHER PUBLICATIONS

Gritzali et al., *Chemical Abstracts*, vol. 93, Abstract No. 21423a.
Churilova et al., *Chemical Abstracts*, vol. 93, Abstract No. 21382m.
Broome et al., 1978, PNAS, 75(6):2746-2749.
Montenecourt, B. S., *Trends in Biotechnology* 1:156-161 (1983).
Enari, T.-M., *Microbial Cellulases* pp. 183-223, In: Microbiol, Enzymes and Biotechnologies, Wm. M. Fogart (ed) Applied Science Publication, London and New York.
Shoemaker, S. P. et al., *Biochim. Biophys. Acta* 523:133-146 (1978).
Shoemaker, S. P. et al., *Biochim. Biophys. Acta* 523:147-161 (1978).
Fägerstam, L. G. et al., *FEBS Letters* 98:363-367 (1979).
Fägerstam, L. G. et al., *FEBS Letters* 119:97-100 (1980).
Sprey, B. et al., *FEMS Microbial Letters* 18:217-222 (1983).
Nummi, M. et al., *Biochim. J.* 215:677-683 (1983).

(List continued on next page.)

*Primary Examiner*—Richard A. Schwartz
*Assistant Examiner*—J. LeGuyader
*Attorney, Agent, or Firm*—Sterne, Kessler, Goldstein & Fox

[57] ABSTRACT

Methods and means for the construction of strains of yeast capable of producing cellulolytic enzymes, achieved by the transfer of chromosomal genes or cDNA copies of mRNAs coding for cellulolytic enzymes isolated from the fungus *Trichoderma reesei* to yeast cells using recombinant DNA vectors capable of replicating in yeast. The correct expression of these cellulolytic genes in yeast leads to the production of cellulolytic enzymes which are secreted from the cell. This allows the yeast to hydrolyze 3-1,4-glucan substrates such as cellulose.

16 Claims, 16 Drawing Sheets

OTHER PUBLICATIONS

Shoemaker, S. et al., *Bio/Technology*, 1:691–696 (1983).
Teeri, T. et al., *Bio/Technology* 1:696–699 (1983).
Raynal, A. et al., *Mol. Gen. Genet.* 195:108–115 (1984).
Mandels, M. et al., *Appl. Microbiol.* 21:152–154 (1971).
Picataggio et al., *Abst. Annu. Meet of Am. Soc. Microbiol.* 81: (1981); Abstract H19.
Shoemaker et al., *World Biotech. Rep.* 2:593–600 (1984).
Van Arsdell, J. N. et al., *Bio/Technology* 5:60–64 (1987).
Penttilä, M. E. et al., *Yeast* 3:175–185 (1987).
Penttilä, M. E., et al., *Gene* 45:253–263 (1986).
Saloheimo, M. et al. *Gene* 63:11–21 (1988).
Chanzy, H. et al., *FEBS Letters* 153(1):113–118 (1983).
Mellor, J. et al., *Gene* 24:1–14 (1983).
Thomsen, K. K., Carlsberg Res. Commun. 48:545–555 (1983).
Nevalainen, K. M. H., *App. Env. Microbiol.* 41(3):593–596 (1981).
Bailey, M. J. et al., *Enzyme Microb. Technol.* 3:153–157 (Apr. 1981).
Pettersson, G., et al., Institute of Biochemistry, University of Uppsala, 111:39–42.
Henrissat, B. et al., *Biotechnology* 3:722–726 (1985).
Chen, C. M. et al., *Biotechnology* 5:74–77 (1987).
van Tilbeurgh, H. et al., *FEBS* 1375 169(2):215–218 (1984).
Gong, Cheng-Shung, et al., *Adv. Chem. Ser.* 181:261–287 (1979).
Shoemaker, S. et al., *Biotechnology* pp. 687–690 (1983).
James, A. P. et al., Third Bioenergy R&D Seminar, Mar. 24–25, 1981, pp. 135–139.
Kubicek, C. P. et al, "The Trichoderma cellulase regulatory puzzle: From the Interior life of a secretory fungus," *Enzyme Microb. Technol.* 15:90–99 (Feb. 1993).
Heijne, G. V., "A new method for predicting signal sequence cleavage sites," *Nucl. Acids Res.* 14(11):4683–4689 (1986).
Bhikhabhai, R. et al., "The cellulolytic enzymes of *Trichoderma reesei* as a system of homologous proteins," *FEBS Letts.* 167(2):301–308 (Feb. 1984).

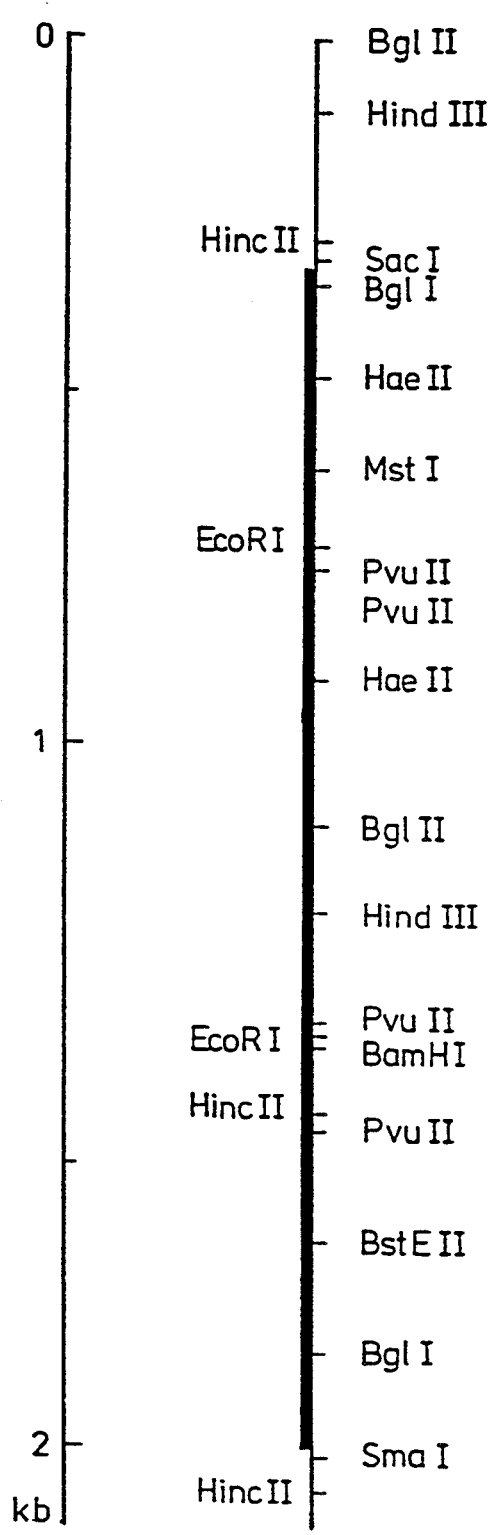
- FIGURE 1 -

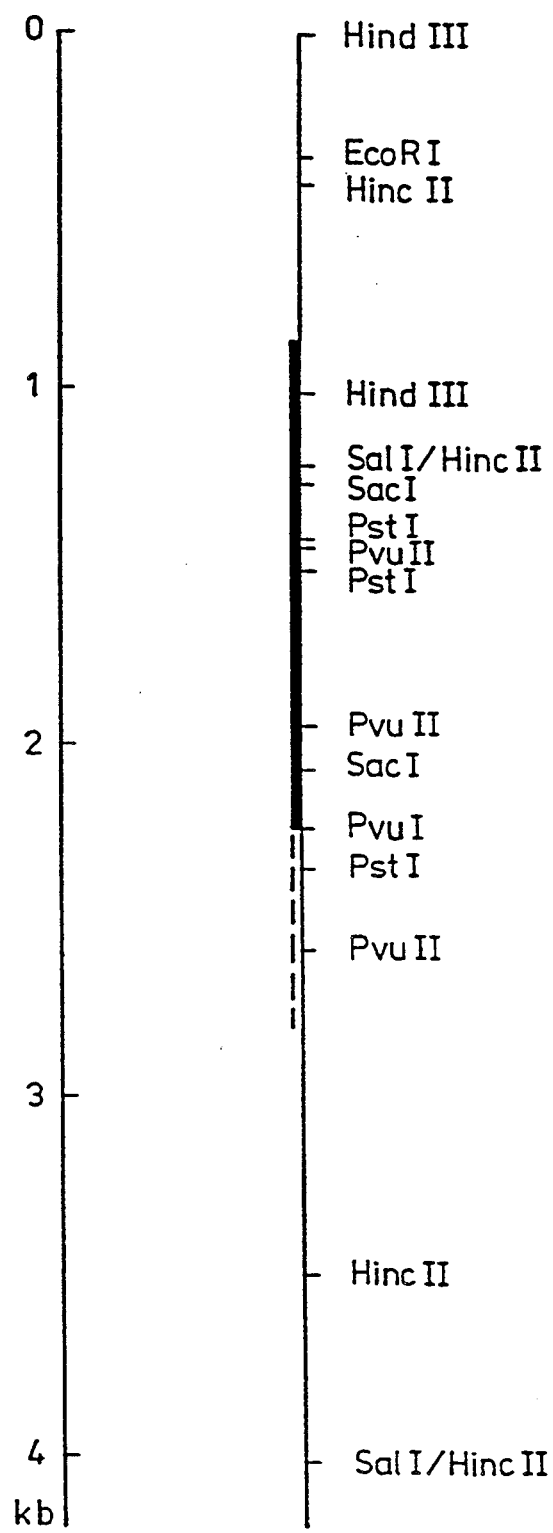
- FIGURE 2 -

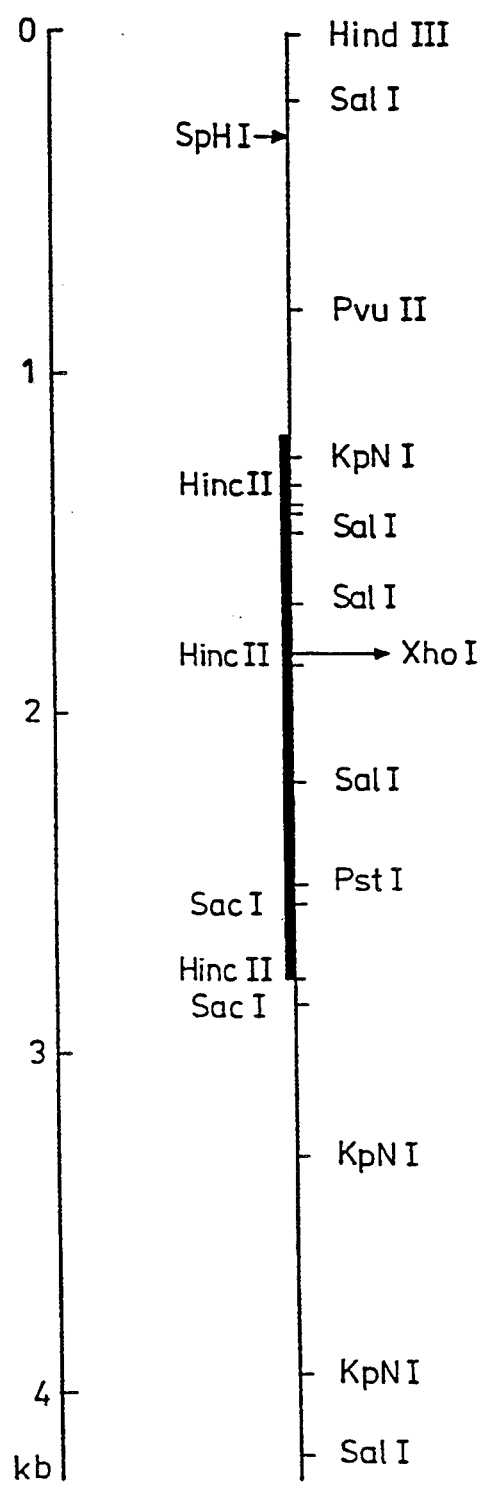
- FIGURE 3 -

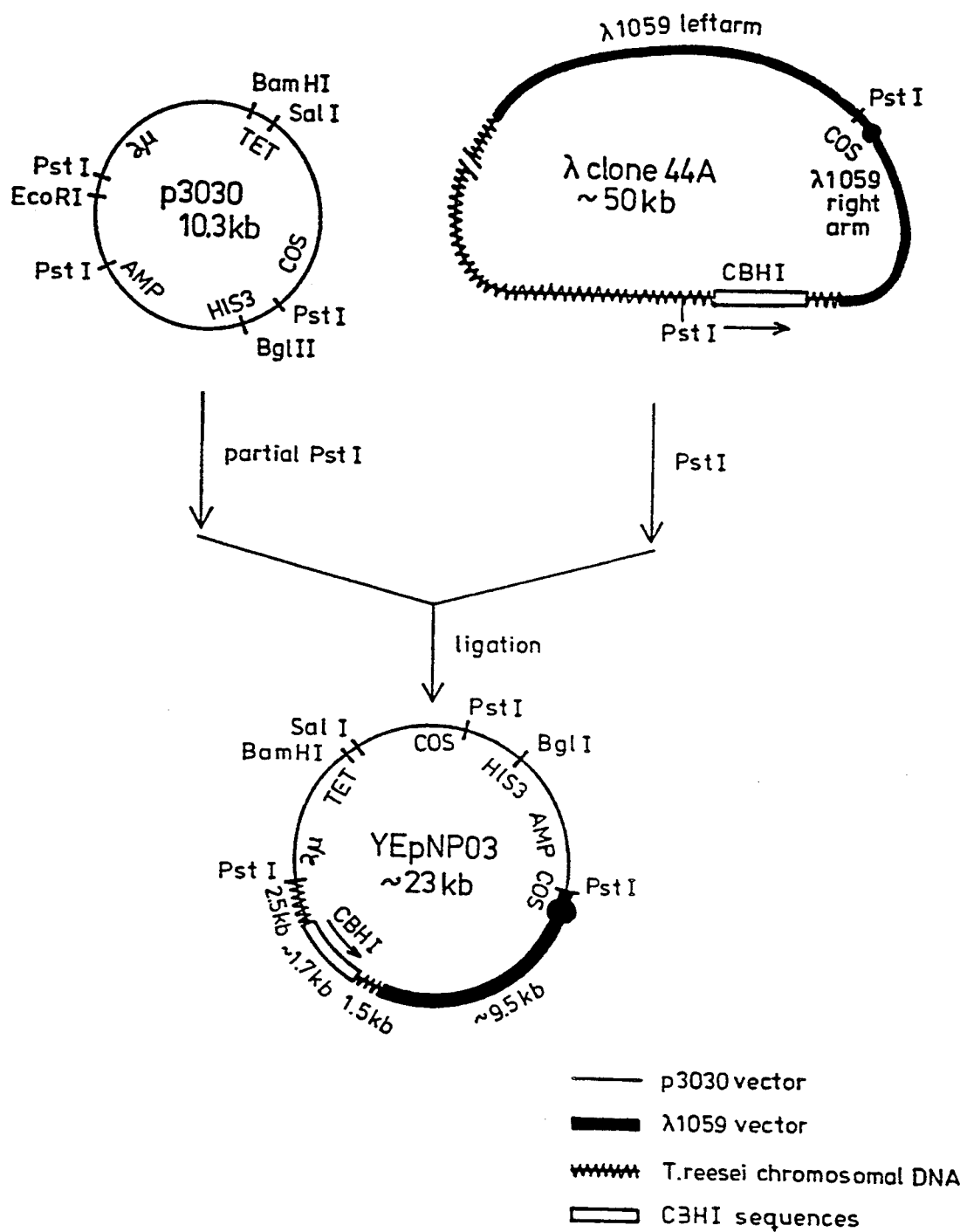
- FIGURE 4 -

```
                                    EcoRI    CBH II CDNA
                              ACCATGATTACGAATTCCCCTTGTAAGATCACCCTCTGTGTATTGCACC
                                             ←
                                           pUC8
┌─CBH II signal sequence─────────────────────────────────────────┐Hind III
ATGATTGTCGGCATTCTCACCACGCTGGCTACGCTGGCCACACTCGCAGCTAGTGTGCCTCTAGAGGAGCGGCAAGCTTGCTCAAGCGTC
MetIleValGlyIleLeuThrThrLeuAlaThrLeuAlaThrLeuAlaAlaSerValProLeuGluGluArgGlnAlaCysSerSerVal      30
                                                              CBHII mature protein
                               Acc I
TGGGGCCAATGTGGTGGCCAGAATTGGTCGGGTCCGACTTGCTGTGCTTCCGGAAGCACATGCGTCTACTCCAACGACTATTACTCCCAG
TrpGlyGlnCysGlyGlyGlnAsnTrpSerGlyProThrCysCysAlaSerGlySerThrCysValTyrSerAsnAspTyrTyrSerGln    60

Acc I                                         Sac I
TGTCTTCCCGGCGCTGCAAGCTCAAGCTCGTCCACGCGCGCCGCGTCGACGACTTCTCGAGTATCCCCCACAACATCCCGGTCGAGCTCC
CysLeuProGlyAlaAlaSerSerSerSerSerThrArgAlaAlaSerThrThrSerArgValSerProThrThrSerARgSerSerSer    90

GCGACGCCTCCACCTGGTTCTACTACTACCAGAGTACCTCCAGTCGGATCGGGAACCGCTACGTATTCAGGCAACCCTTTTGTTGGGGTC
AlaThrProProProGlySerThrThrThrArgValProProValGlySerGlyThrAlaThrTyrSerGlyAsnProPheValGlyVal  120

Pst I Pvu II
ACTCCTTGGGCCAATGCATATTACGCCTCTGAAGTTAGCAGCCTCGCTATTCCTAGCTTGACTGGAGCCATGGCCACTGCTGCAGCAGCT
ThrProTrpAlaAsnAlaTyrTyrAlaSerGluValSerSerLeuAlaIleProSerLeuThrGlyAlaMetAlaThrAlaAlaAlaAla  150

GTCGCAAAAGGTTCCCTCTTTTATGTGGCTAGATACTCTTGACAAGACCCCTCTCATGGAGCAAACCTTGGCCGACATCCGCACCGCCAAC
ValAlaLysValProSerPheMetTrpLeuAspThrLeuAspLysThrProLeuMetGluGlnThrLeuAlaAspIleArgThrAlaAsn  180

AAGAATGGCGGTAACTATGCCGGACAGTTTGTGGTGTATGACTTGCCGGATCGCGATTGCGCTGCCCTTGCCTCGAATGGCGAATACTCT
LysAsnGlyGlyAsnTyrAlaGlyGlnPheValValTyrAspLeuProAspArgAspCysAlaAlaLeuAlaSerAsnGlyGluTyrSer  210

ATTGCCGATGGTGGCGTCGCCAAATATAAGAACTATATCGACACCATTCGTCAAATTGTCGTGGAATATTCCGATATCCGGACCCTCCTG
IleAlaAspGlyGlyValAlaLysTyrLysAsnTyrIleAspThrIleArgGlnIleValValGluTyrSerAspIleArgThrLeuLeu  240

GTTATTGAGCCTGACTCTCTTGCCAACCTGGTGACCAACCTCGGTACTCCAAAGTGTGCCAATGCTCAGTCAGCCTACCTTGAGTGCATC
ValIleGluProAspSerLeuAlaAsnLeuValThrAsnLeuGlyThrProLysCysAlaAsnAlaGlnSerAlaTyrLeuGluCysIle  270

Pvu II
AACTACGCCGTCACACAGCTGAACCTTCCAAATGTTGCGATGTATTTGGACGCTGGCCATGCAGGATGGCTTGGCTGGCCGGCAAACCAA
AsnTyrAlaValThrGlnLeuAsnLeuProAsnValAlaMetTyrLeuAspAlaGlyHisAlaGlyTrpLeuGlyTrpProAlaAsnGln  300

Sac I
GACCCGGCCGCTCAGCTATTTGCAAATGTTTACAAGAATGCATCGTCTCCGAGAGCTCTTCGCGGATTGGCAACCAATGTCGCCAACTAC
AspProAlaAlaGlnLeuPheAlaAsnValTyrLysAsnAlaSerSerProArgAlaLeuArgGlyLeuAlaThrAsnValAlaAsnTyr  330
```

FIG.5A

```
                                                            Acc I
AACGGGTGGAACATTACCAGCCCCCCATCGTACACGCAAGGCAACGCTGTCTACAACGAGAAGCTGTACATCCACGCTATTGGACCTCTT
AsnGlyTrpAsnIleThrSerProProSerTyrThrGlnGlyAsnAlaValTyrAsnGluLysLeuTyrIleHisAlaIleGlyProLeu      360

Pvu I
CTTGCCAATCACGGCTGGTCCAACGCCTTCTTCATCACTGATCAAGGTCGATCGGGAAAGCAGCCTACCGGACAGCAACAGTGGGGAGAC
LeuAlaAsnHisGlyTrpSerAsnAlaPhePheIleThrAspGlnGlyArgSerGlyLysGlnProThrGlyGlnGlnGlnTrpGlyAsp      390

TGGTGCAATGTGATCGGCACCGGATTTGGTATTCGCCCATCCGCAAACACTGGGGACTCGTTGCTGGATTCGTTTGTCTGGGTCAAGCCA
TrpCysAsnValIleGlyThrGlyPheGlyIleArgProSerAlaAsnThrGlyAspSerLeuLeuAspSerPheValTrpValLysPro      420

GGCGGCGAGTGTGACGGCACCAGCGACAGCAGTGCGCCACGATTTGACTCCCACTGTGCGCTCCCAGATGCCTTGCAACCGGCGCCTCAA
GlyGlyGluCysAspGlyThrSerAspSerSerAlaProArgPheAspSerHisCysAlaLeuProAspAlaLeuGlnProAlaProGln      450

STOP
GCTGGTGCTTGGTTCCAAGCCTACTTTGTGCAGCTTCTCACAAACGCAAACCCATCGTTCCTGTAAGGCTTTCGTGACCGGGCTTCAAAC
AlaGlyAlaTrpPheGlnAlaTyrPheValGlnLeuLeuThrAsnAlaAsnProSerPheLeu                                  471

Acc I
AATGATGTGCGATGGTGTGGTTCCCCGGTTCGCGGAGTCTTTGTCTACTTTGGTTGTCTGTCGCAGGTCGGTAGACCGCAAATGAGCAACT

GATGGATTGTTGCCAGCGATACTATAATTCACATGGATGGTCTTTGTCGATCAGTAGGCTAGAGAGAGAGAGAGAACATCTATCCACAAT polyA   Bam HI
GTCGAGTGTCTATT(A)₁₃ GGGGATCC
                    pUC8
```

FIG.5B

```
                              pUC8
                        ←――――――
                                    CCCCCCTATCTTAGTCCTTCTTGTTGTCCCAAA

┌――――――ENDO II signal   sequence――――――――――――――┐   Kpn I
ATGGCGCCCTCAGTTACACTGCCGTTGACCACGGCCATCCTGGCNATTGCCCGGCTCGTCGCCGCCCAGCAACCGGGTACCAGCACCCCC
MetAlaProSerValThrLeuProLeuThrThrAlaIleLeuAlaIleAlaArgLeuValAlaAlaGlnGlnProGlyThrSerThrPro   30

GAGGTCCATCCCAAGTTGACAACCTACAAGTGTACAAAGTCCGGGGGGTGCGTGGCCCAGGACACCTCGGTGGTCCTTGACTGGAACTAC
GluValHisProLysLeuThrThrTyrLysCysThrLysSerGlyGlyCysValAlaGlnAspThrSerValValLeuAspTrpAsnTyr   60

CGCTGGATGCACGACGCAAACTACAACTCGTGCACCGTCACCGGCGCGTCAACACCACGCTCTGCCCTGACGAGGCGACCTGTGGCAAG
ArgTrpMetHisAspAlaAsnTyrAsnSerCysThrValAsnGlyGlyValAsnThrThrLeuCysProAspGluAlaThrCysGlyLys   90

Sal I
AACTGCTTCATCCAGGGCGTCGACTACGCCGCCTCGGGCGTCACCACCTCGGGCAGCAGCCTCACCATGAACCAGTACATGCCCAGCAGC
AsnCysPheIleGlnGlyValAspTyrAlaAlaSerGlyValThrThrSerGlySerSerLeuThrMetAsnGlnTyrMetProSerSer  120

TCTGGCGGCTACAGCAGCGTCTCTCCTCGGCTGTATCTCCTGGACTCTGACGGTGAGTACGTGATGCTGAAGCTCAACGGCCAGGAGCTG
SerGlyGlyTyrSerSerValSerProArgLeuTyrLeuLeuAspSerAspGlyGluTyrValMetLeuLysLeuAsnGlyGlnGluLeu  150

Sal I
AGCTTCGACGTCGACCTCTCTGCTCTGCCCGTGTGGAGAGAACGGCTCGCTCTACCTGTCTCAGATGGACGAGAACGGGGGCGCCAACCAG
SerPheAspValAspLeuSerAlaLeuProCysGlyGluAsnGlySerLeuTyrLeuSerGlnMetAspGluAsnGlyGlyAlaAsnGln  180

TATAACACGGCCGGTGCCAACTACGGGAGCGGCTACTGCGATGCTCAGTGCCCCGTCCAGACATGGAGGAACGGCACCCTCAACACTAGC
TyrAsnThrAlaGlyAlaAsnTyrGlySerGlyTyrCysAspAlaGlnCysProValGlnThrTrpArgAsnGlyThrLeuAsnThrSer  210

Xho I
CACCAGGGCCAGGGCTTCTGCTGCAACGAGATGGATATCCTGGAGGGCAACTCGAGGGCGAATGCCTTGACCCCTCACTCTTGCACGGCC
HisGlnGlyGlnGlyPheCysCysAsnGluMetAspIleLeuGluGlyAsnSerArgAlaAsnAlaLeuThrProHisSerCysThrAla  240

ACGGCCTGCGACTCTGCCGGTTGCGGCTTCAACCCCTATGGCAGCGGCTACAAAAGCTACTACGGCCCCGGAGATACCGTTGACACCTCC
ThrAlaCysAspSerAlaGlyCysGlyPheAsnProTyrGlySerGlyTyrLysSerTyrTyrGlyProGlyAspThrValAspThrSer  270

AACACCTTCACCATCATCACCCAGTTCAACACGGACAACGGCTCGCCCTCGGGCAACCTTGTGAGCATCACCCGCAAGTACCAGXXXXXX
LysThrPheThrIleIleThrGlnPheAsnThrAspAsnGlySerProSerGlyAsnLeuValSerIleThrArgLysTyrGln......  300

Sal I
GTCGACATCCCCAGCGCCCAGCCCGGCGGCGACACCATCTCGTCCTGCCCGTCCGCCTCAGCCTACGGCGGCCTCGCCACCATGGGCAAG
ValAspIleProSerAlaGlnProGlyGlyAspThrIleSerSerCysProSerAlaSerAlaTyrGlyGlyLeuAlaThrMetGlyLys  330

GCCCTGAGCAGCGGCATGGTGCTCGTGTTCAGCATTTGGAACGACAACAGCCAGTACATGAACTGGCTCGACAGCGGCAACGCCGGCCCC
AlaLeuSerSerGlyMetValLeuValPheSerIleTrpAsnAspAsnSerGlnTyrMetAsnTrpLeuAspSerGlyAsnAlaGlyPro  360
```

FIG.6A

```
Pst I
TGCAGCAGCACCGAGGGCAACCCATCCAACATCCTGGCCAACAACCCCAACACGCACGTCGTCTTCTCCAACATCCGCTGGGGAGACATT
CysSerSerThrGluGlyAsnProSerAsnIleLeuAlaAsnAsnProAsnThrHisValValPheSerAsnIleArgTrpGlyAspIle      390

Sac I
GGGTCTACTACGAACTCGACT....x......x..GAGCTCGACGACTTCGAGCAGCCCGAGCTGCACGCAGACTCACTGGGGGCAGTGC
GlySerThrThrAsnSerThr...............SerSerThrThrSerSerSerProSerCysThrGlnThrHisTrpGlyGlnCys    420
                                                                        ↓           STOP
GGTGGCATTGGGTACAGCGGGTGCAAGACGTGCACGTCGGGCACTACGTGCCAGTATAGCAACGACTACTACTCGCAATGCCTTTAGAGC
GlyGlyIleGlyTyrSerGlyCysLysThrCysThrSerGlyThrThrCysGlnTyrSerAsnAspTyrTyrSerGlnCysLeuxxx       450

Sac I
GTTGACTTGCCTCTGGTCTGTCCAGACGGGGGCACGATAGAATGCGGGCACGCAGGGAGCTCGTAGACATTGGGCTTAATATATAAGACA

POLY A  pUC8
TGCTATGTTGTATCTACATTAGCAAATGACAAACAAATGAAAAAGAACTTATCAAGC(A)₂₅
```

FIG.6B

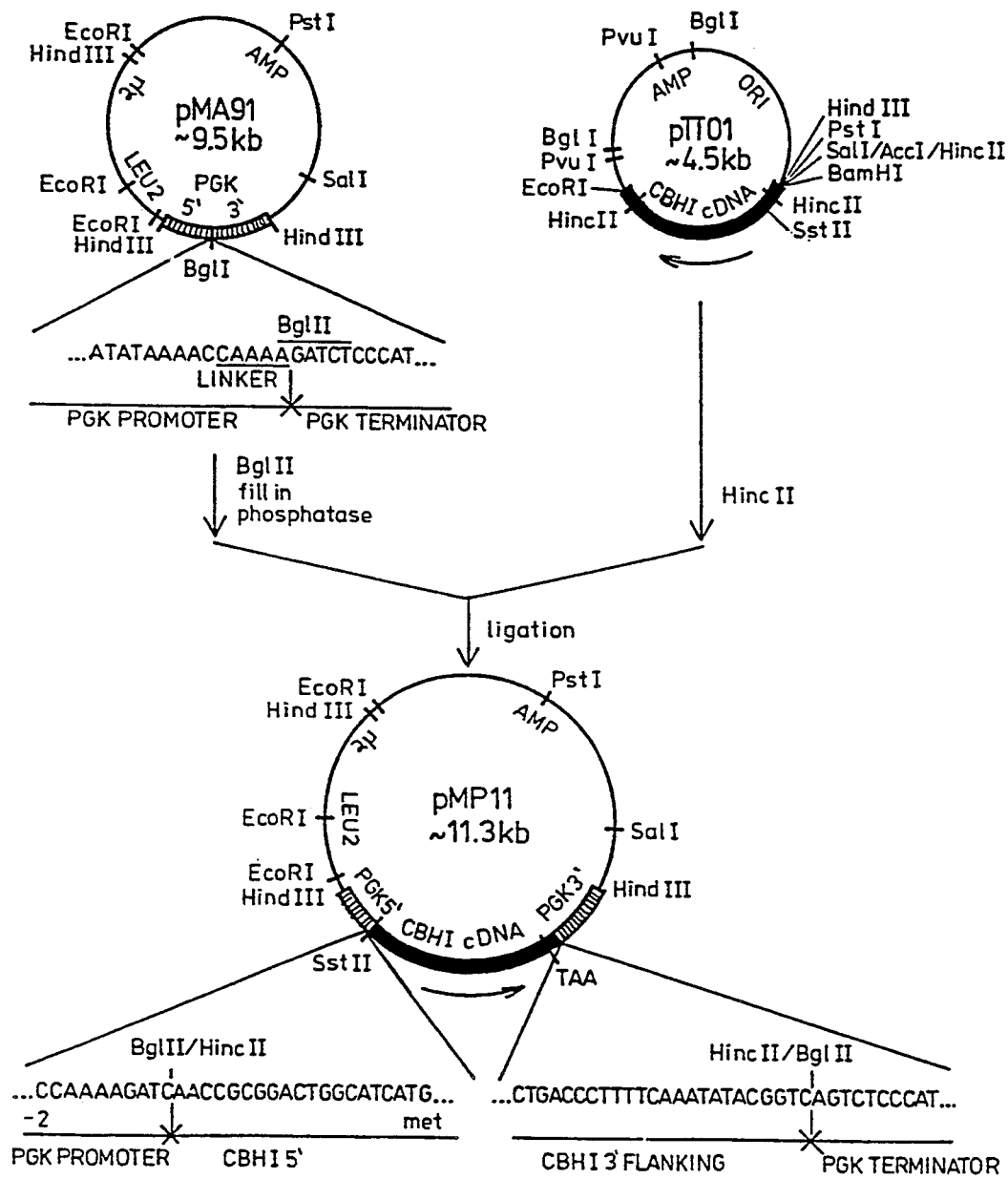
- FIGURE 7 -

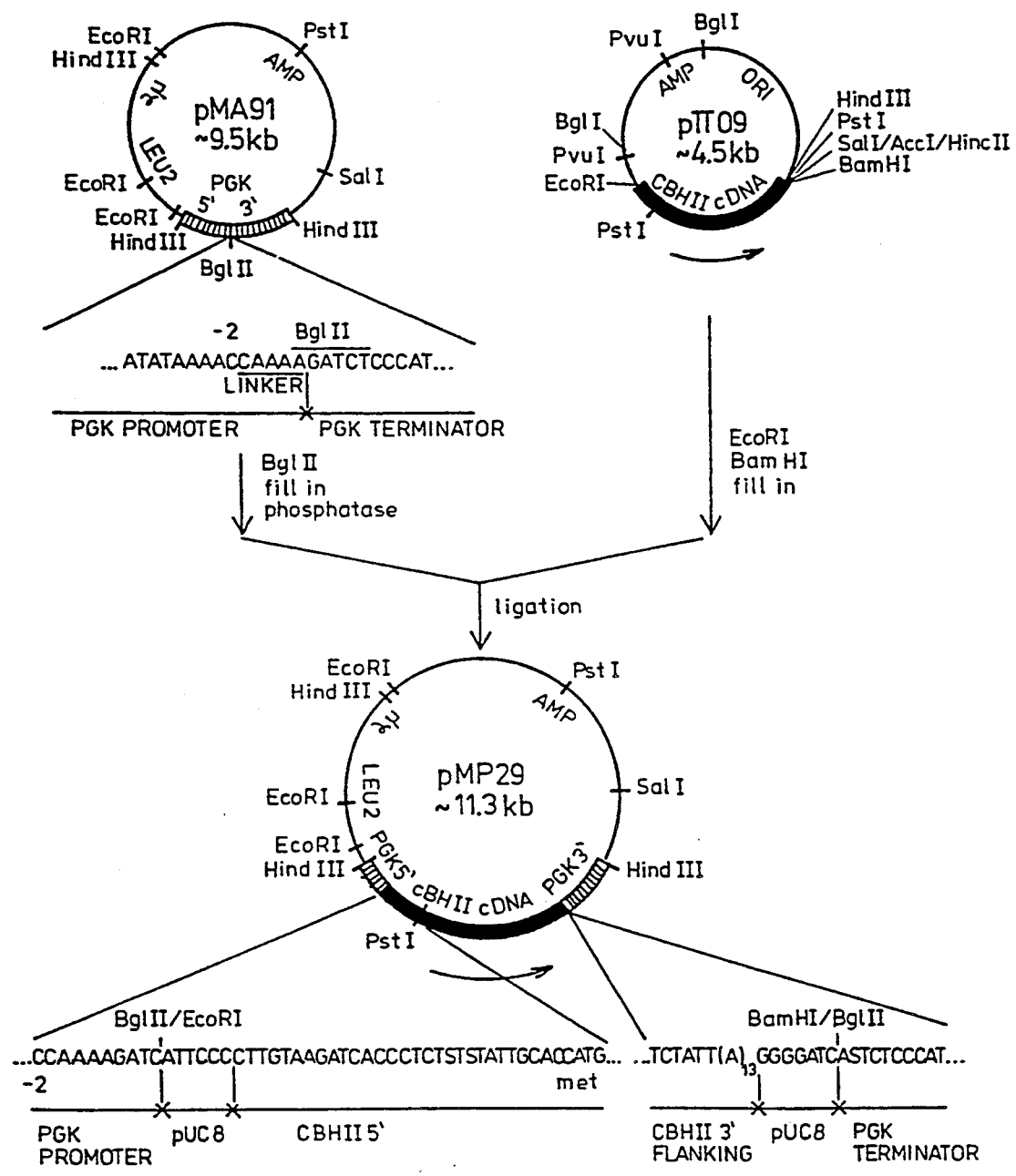
- FIGURE 8 -

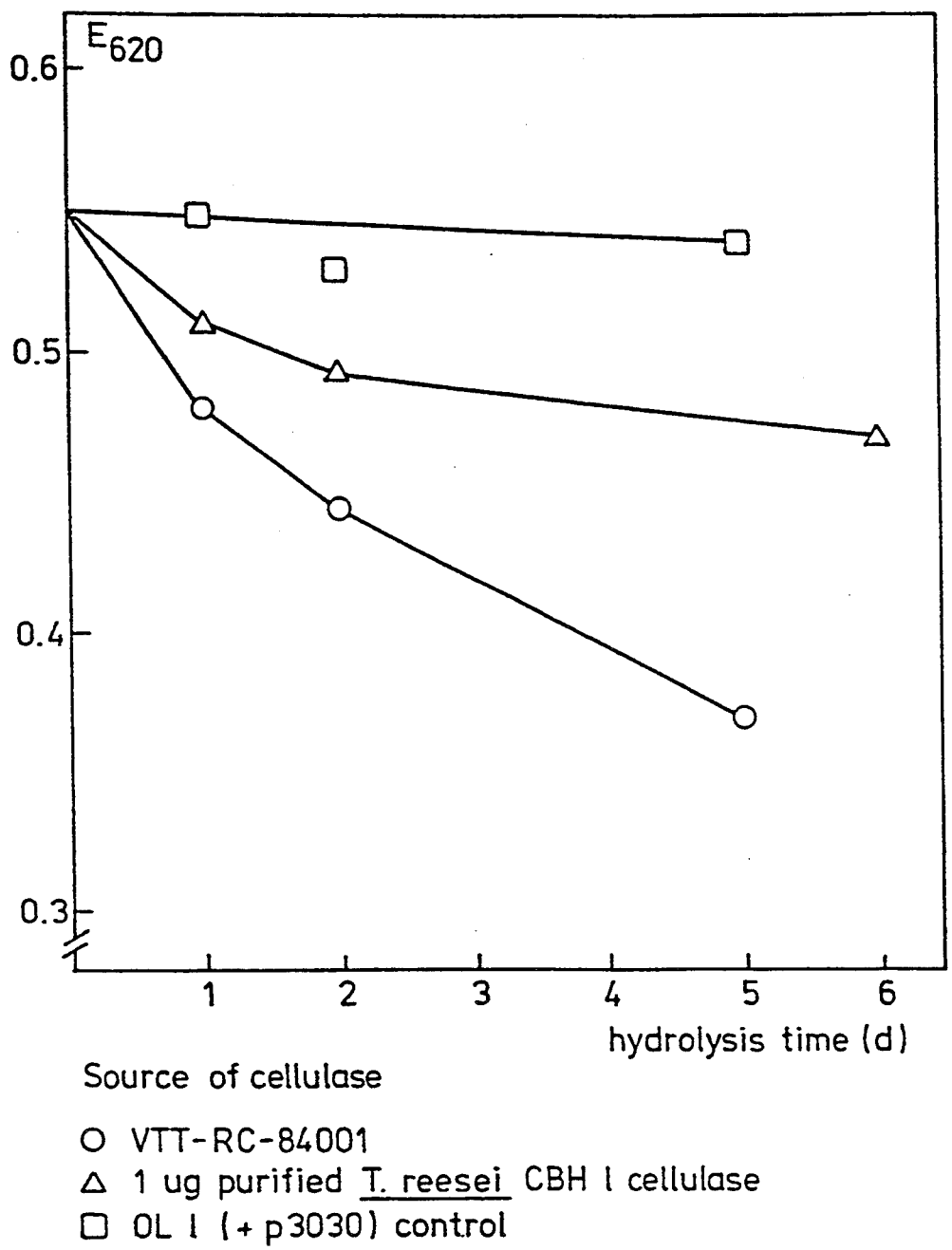
- FIGURE 10 -

```
               1                                                          10                                              20
               Met Ala Pro Ser Val Thr Leu Pro Leu Thr Thr Ala Ile Leu Ala Ile Ala Arg Leu Val Ala Ala Gln Pro Gly Thr
TTGTCCCAAA     ATG GCG CCC TCA GTT ACA CTG CCG CTG ACC ACG GCC ATC CTG GCC ATT GCC CGG CTC GTC GCC GCC CAG CAA CCC GGT ACC
                                                                                                                   Kpn I
         30                                              40                                              50
Ser Thr Pro Glu Val His Pro Lys Leu Thr Thr Tyr Lys Ser Gly Gly Cys Val Ala Gln Asp Thr Ser Val Val Leu Asp
AGC ACC CCC GAG GTC CAT CCC AAG TTG ACA ACC TAC AAG TCC GGG GGG TGC GTG GCC CAG GAC ACC TCG GTC GTC CTT GAC 60                                              70                                              80
Trp Asn Tyr Arg Trp Met His Asp Ala Asn Tyr Asn Ser Cys Thr Val Asn Gly Gly Val Asn Thr Thr Leu Cys Pro Asp Glu Ala Thr
TGG AAC TAC CGC TGG ATG CAC GAC GCA AAC TAC AAC TCG TGC ACC GTC AAC GGC GGT GTC AAC ACC ACC CTC TGC CCT GAC GAG GCG ACC 90                                              100                                             110
Cys Gly Lys Asn Cys Phe Ile Glu Gly Val Asp Tyr Ala Ala Ser Gly Val Thr Thr Ser Gly Ser Ser Leu Thr Met Asn Gln Tyr Met
TGT GGC AAG AAC TGC TTC ATC GAG GGC GTC GAC TAC GCC GCC AGC GGC GTC ACC ACC TCG GGC AGC AGC CTC ACC ATG AAC CAG TAC ATG 120                                             130                                             140
Pro Ser Ser Gly Gly Tyr Ser Ser Val Ser Pro Arg Leu Tyr Leu Leu Asp Ser Asp Gly Glu Tyr Val Met Leu Lys Leu Asn Gly
CCC AGC AGC GGC GGC TAC AGC AGC GTC TCT CCT CGG CTC TAT CTC CTG GAC TCT GAC GGT GAG TAC GTC ATG CTC AAG CTC AAC GGC
                                               Sal I 150                                             160                                             170
Gln Glu Leu Ser Phe Asp Val Asp Leu Ser Ala Leu Pro Cys Gly Glu Asn Gly Ser Leu Tyr Leu Ser Gln Met Asp Glu Asn Gly Gly
CAG GAG CTG AGC TTC GAC GTC GAC CTG TCT GCT CTG CCG TGT GGA GAG AAC GGC TCG CTC TAC CTG TCT CAG ATG GAC GAG AAC GGG GGC
                                  Sal I 180                                             190                                             200
Ala Asn Gln Tyr Asn Thr Ala Gly Ala Asn Tyr Gly Ser Gly Tyr Cys Asp Ala Gln Cys Pro Val Gln Thr Trp Arg Asn Gly Thr Leu
GCC AAC CAG TAT AAC ACG GCC GGT GCC AAC TAC GGG AGC GGC TAC TGC GAT GCT CAG TGC CCC GTC CAG ACA TGG AGG AAC GGC ACC CTC
                                                                                                      *
```

FIG.11A

```
*    210
Asn Thr Ser His Gln Gly Phe Cys Cys Asn Glu Met Asp Ile Leu Glu Gly Asn Ser Arg Ala Asn Ala Leu Thr Pro His Ser Cys Thr
AAC ACT AGC CAC CAG GGC TTC TGC TGC AAC GAG ATG GAT ATC CTG GAG GGC AAC TCG AGG GCG AAT GCC TTG ACC CCT CAC TCT TGC ACG
                                                                          220                    Xho I        230

240                                                      250                                              260
Ala Thr Ala Cys Asp Ser Ala Gly Cys Gly Phe Asn Pro Tyr Gly Ser Gly Tyr Lys Ser Tyr Tyr Gly Pro Gly Asp Thr Val Asp Thr
GCC ACG GCC TGC GAC TCT GCC GGT TGC GGC TTC AAC CCC TAT GGC AGC GGC TAC AAA AGC TAC TAC GGC CCC GGA GAT ACC GTT GAC ACC 270                                       280  *                                     290
Ser Lys Thr Phe Thr Ile Ile Thr Gln Phe Asn Thr Asp Asn Gly Ser Pro Ser Gly Asn Leu Val Ser Ile Thr Arg Lys Tyr Gln Gln
TCC AAG ACC TTC ACC ATC ATC ACC CAG TTC AAC ACG GAC AAC GGC TCG CCC TCG GGC AAC CTT GTG AGC ATC ACC CGC AAG TAC CAG CAA

300                            Sal I                    310                                              320
Asn Gly Val Asp Ile Pro Ser Ala Gln Pro Gly Gly Asp Thr Ile Ser Ser Cys Pro Ser Ala Ser Ala Tyr Gly Gly Leu Ala Thr Met
AAC GGC GTC GAC ATC CCC AGC GCC CAG CCC GGC GGC GAC ACC ATC TCG TCC TGC CCG TCC GCC TCA GCC TAC GGC GGC CTC GCC ACC ATG 330                                                      340                                              350
Gly Lys Ala Leu Ser Ser Gly Met Val Leu Val Phe Ser Ile Trp Asn Asp Asn Ser Gln Tyr Met Asn Trp Leu Asp Ser Gly Asn Ala
GGC AAG GCC CTG AGC AGC GGC ATG GTG CTC GTG TTC AGC ATT TGG AAC GAC AAC AGC CAG TAC ATG AAC TGG CTC GAC AGC GGC AAC GCC 360                                                      370                                              380
Gly Pro Cys Ser Ser Thr Glu Gly Asn Pro Ser Asn Ile Leu Ala Asn Asn Pro Asn Thr His Val Val Phe Ser Asn Ile Arg Trp Gly
GGC CCC TGC AGC AGC ACC GAG GGC AAC CCA TCC AAC ATC CTG GCC AAC AAC CCC AAC ACC CAC GTC GTC TTC TCC AAC ATC CGC TGG GGA
Pst I
```

FIG.11B

```
        390                   400                                          410
Asp Ile Gly Ser Thr Thr Asn Ser Thr Ala Pro Pro Pro Ser Thr Thr Phe Ser Thr Thr Arg Arg Ser Ser Thr Thr
GAC ATT GGG TCT ACT ACG AAC TCG ACT GCG CCT CCC CCG TCC AGC ACG ACG TTT TCG ACT ACA CGG AGG AGC TCG ACG ACT
                                                                                        ─────────
                                                                                          Sac I 420                   430                                          440
Ser Ser Ser Pro Ser Cys Thr Gln Thr His Trp Gly Gly Gly Ile Gly Tyr Ser Gly Cys Lys Thr Cys Thr Ser Gly Thr
TCG AGC AGC CCC AGC TGC ACG CAG ACT CAC TGG GGG CAG TGC GGT GGC ATT GGG TAC AGC GGG TGC AAG ACG TCG GGC ACT ACG 450             459
Cys Gln Tyr Ser Asn Asp Tyr Tyr Ser Gln Cys Leu
TGC CAG TAT AGC AAC GAC TAC TAC TCG CAA TGC CTT TAG AGCCTTGACT
```

FIG.11C 5,393,670

DNA, VECTORS AND TRANSFORMED HOSTS ENCODING *TRICHODERMA REESEI* ENDOGLUCANASE I

This application is a continuation of application Ser. No. 07/418,154, filed Oct. 6, 1989, now abandoned, which is a division of application Ser. No. 06/817,942, filed Jan. 30, 1986, now U.S. Pat. No. 4,894,338.

BACKGROUND OF THE INVENTION

Three different classes of enzymatic activity have been shown to be required for the complete hydrolysis of cellulose to glucose. The two major activities involved in cellulose solubilization are endoglucanase (EC 3.2.1.4) and cellobiohydrolase (EC 3.2.1.91) (1, 2). For the production of glucose a third type of activity, cellobiase or β-glucosidase (EC 3.2.1.21) is also required. The precise manner in which these three different classes of enzyme interact to bring about the complete hydrolysis of cellulose is not yet clear.

Some filamentous fungi produce a number of different isoenzymes of each class of cellulolytic enzyme which apparently interact synergistically in hydrolysis (3, 4, 5, 6).

Trichoderma has been shown to produce at least two immunologically distinct cellobiohydrolases CBH I and CBH II, at least 2 endoglucanases, ENDO II and ENDO III, and a β-glucosidase. ENDO II and ENDO III are now known as EGI and EGII, respectively. While enzymatic hydrolysis of cellulose proceeds most rapidly in the presence of all these enzymes, CBH I alone is able to degrade crystalline cellulose to glucose and cellobiose (7, 8, 9).

Two groups have reported the molecular cloning of the *T. reesei* gene for CBH I and the complete sequence of this gene is known (10, 11).

Yeast is an important industrial organism and is used for brewing, wine making, baking, ethanol production, single cell protein production and more recently for the production of pharmaceuticals such as interferon, growth hormone and Hepatitis B virus antigen. Yeast do not produce enzymes that degrade cellulose. The development of yeast strains able to hydrolyse cellulose would make possible improvements in existing processes where cellulose or glucans are present in the raw material used. As important would be the possibility of developing new processes not currently possible.

In filtration and clarification of beer high molecular weight β-glucans originating from barley grain cause problems. In the brewing industry microbial β-glucanases are used to remove these β-glucans. If the yeast used in the production of beer were able to produce endoglucanases, the filterability of beer would significantly be improved and the cost of filtering would decrease. By transferring individual fungal cellulase genes to yeast it is possible to produce yeast strains that produce only one cellulase enzyme. Such yeast strains would produce enzymes for use in, for example the pulp and paper industry. Cellulose used in paper making could be swelled by pretreating with one cellulase enzyme, which would bring about swelling without excessive hydrolysis of cellulose.

There are two ways in which a foreign gene can be expressed in yeast. The simplest is to join the whole gene from the chromosome of the donor organism to a yeast vector and transform a yeast cell. If the yeast genetic system recognizes the appropriate sequences in the transferred gene the gene will be expressed. However, in practice this is rare and depends at least in part on the genetic distance between the donor organism and the yeast.

For example, of the five genes from *Aspergillus niger* tested in *Saccharomyces cerevisiae*, only one of these was found to express (12). Therefore it cannot be assumed that heterologous genes will automatically be expressed in yeast.

The second method of obtaining expression of genes in yeast is by connecting either the chromosomal gene or a cDNA copy of the messenger RNA coding for the desired gene to a yeast promotor sequence. In this way, human eukaryote interferon (13), hepatitis B virus surface antigen (14), bovine rennin (15), and mouse α-amylase (16) have all been expressed in yeast.

These and other studies show that while expression of the cDNA or gene is always obtained, the amount and cellular location of the product is very difficult to predict in the absence of experimentation. Montenecourt (1) outlined a number of possible cloning strategies for cloning cellulase genes from *T. reesei* but did not describe the methods to be used to achieve the goal.

SUMMARY OF THE INVENTION

In accordance with this invention described are yeast strains capable of producing cellulolytic enzymes, methods for construction of these strains, recombinant DNA vectors needed in the construction of these strains, methods used in the construction of these vectors, and cDNA copies of cellulolytic enzymes coding genes.

Chromosomal genes coding for three different cellulases, CBH I, CBH II and ENDO II (now EGI) were isolated from a phage gene libary of *T. reesei* by differential hybridization. Fragments of these genes were used to isolate full length cDNAs from a *T. reesei* cDNA libary.

cDNAs for the three cellulases CBH I, CBH II and ENDO II (now EGI) and the CBH I gene were transferred to suitable 2μ yeast plasmids. When used to transform suitable yeast strains, they directed the expression and secretin of the respective cellulase enzyme. The cellulases produced by the yeast were shown to have similar activities to the native fungal enzyme.

A cellulolytic yeast strain *Saccharomyces cerevisiae* VTT-RC-84001 produced in accordance with the present invention has been deposited in the National Collection of Yeast Cultures, Norwich, United Kingdom, under the deposit number NCYC No. R 128 since Apr. 6, 1984.

BRIEF DESCRIPTION OF THE DRAWINGS

The present invention is described below in greater detail with reference to the accompanying drawings.

FIG. 1 shows the restriction map of *T. reesei* cellobiohydrolase I (CBH I) chromosomal gene. The coding region is marked with thickened line.

FIG. 2 shows the restriction map of *T. reesei* cellobiohydrolase II (CBH II) chromosomal gene. The coding region is marked with thickened line.

FIG. 3 shows the restriction map of *T. reesei* endoglucanase II (ENDO II), now endoglucanase I or EGI chromosomal gene. The coding region is marked with thickened line.

FIG. 4 shows the construction of plasmid YEpNP03 for expressior of a chromosomal copy of CBH I gene from *T. reesei* in yeast.

FIG. 5 shows the cDNA sequence of the CBH II gene of *T. reesei* from plasmid pTT09.

FIG. 6 shows the cDNA sequence of the ENDO II (now EGI) gene of *T. reesei* from plasmid Ptt11. The position of introns found in chromosomal copy of the gene are marked with arrow ( ↓ ).

FIG. 7 shows the construction of plasmid pMP11 for expression of *T. reesei* CBH I in yeast.

FIG. 8 shows the construction of plasmid pMP29 for expression of *T. reesei* CBH II in yeast.

FIG. 10 shows the enzyme activity of CBH I produced by the yeast strain VTT-RC-84001.

FIG. 11 shows the primary structure of the egl II (now egl I) gene and ENDO II (now EGI) protein.

DETAILED DESCRIPTION

Figure 9A:
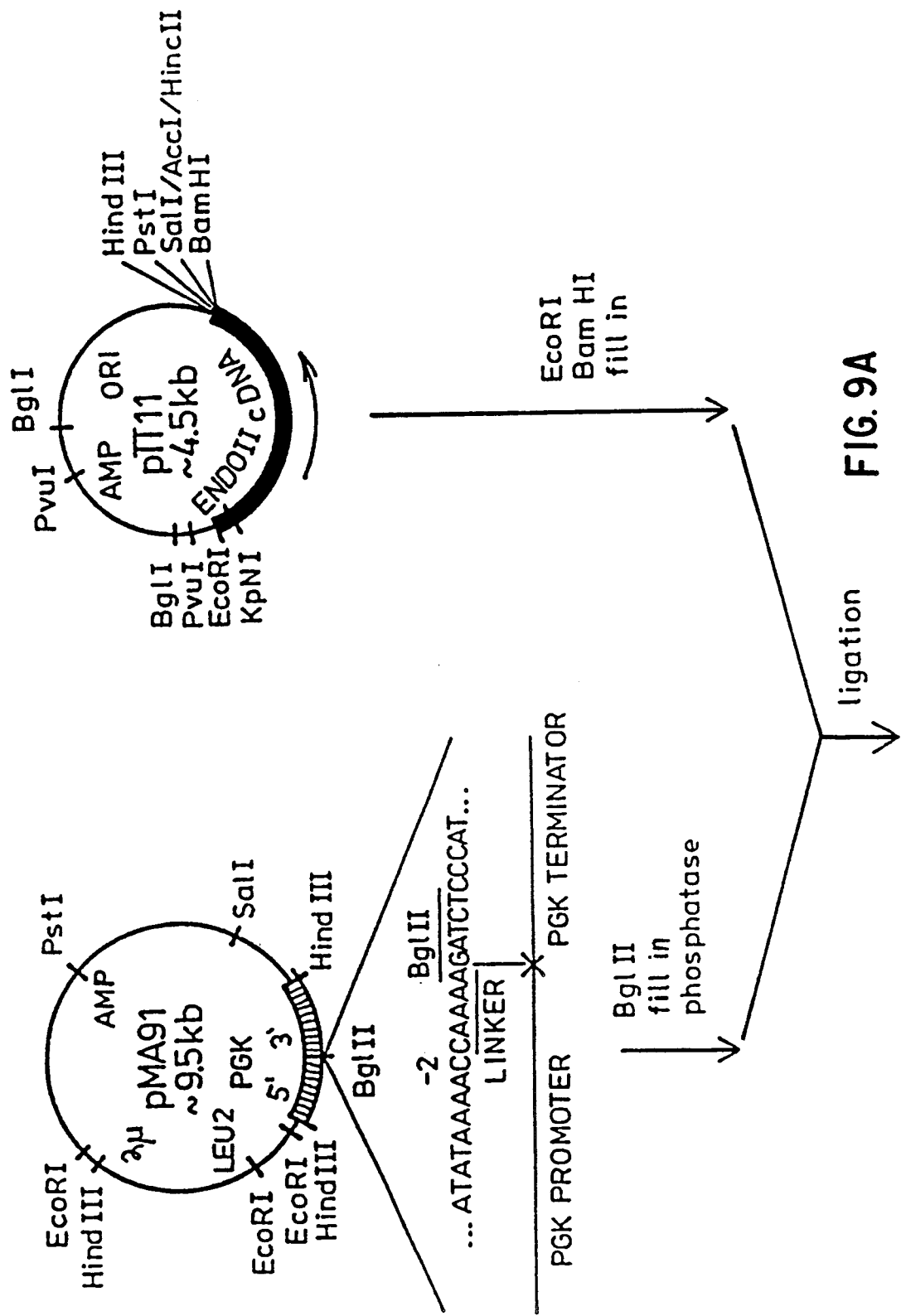
FIG. 9 shows the construction of plasmid pMP311 for expression of *T. reesei* ENDO II (now EGI) in yeast.

The definitions used in this detailed description are as defined in the Gilbert and Talmadge U.S. Pat. No. 4,338,397.

Materials

Bacterial and fungal strains, plasmids, and phage. *T. reesei* strain VTT-D-80133, a mutant strain with improved production of cellulolytic enzymes derived from QM 9414 (17) after several successive mutation steps (18), was used for isolation of the genes from cellobiohydrolase I (CBH I) cellobiohydrolase II (CBH II) and endoglucanase II (ENDO II), now known as endoglucanase I (EGI).

*Escherichia coli* strains Q358 and Q359 and the phage λ1059, used in the construction of the *T. reesei* gene bank were provided by Dr. J. Karn (19). *E. coli* HB 101 was used as a host in 5 transformations with the plasmid pBR 322. *E. coli* JM 101 and the phage M 13 mp 7 (20) and the plasmids pUC 8 and pUC 9 (21), used in the dideoxy sequencing, were from the laboratory of F. Sanger. Yeast strains used were *Saccharomyces cerevisiae* OL1 (Mata leu 2-3 leu 2-112 his 3-11 his 3-15 ura 3-251 ura 3-373) (22) and *S. cerevisiae* MT302-1c (Mata arg 5-6 leu 2-3 leu 2-112 his 3-11 his 3-15 pep 4-3 ade 1) (23).

A 12 kb cosmid p3030 obtained from Barbara Hohn, which replicates both in *E. coli* and in yeast was used as vector for transferring the chromosomal copy of CBH I to yeast. Cosmid p3030 contains genes for ampicillin and tetracycline resistance in *E. coli* and the his3 gene for selection in yeast. The vector contains a cos site which enables it to be packaged into infective λ phage particles in vitro and the yeast 2µ EcoD fragment. Yeast expression vector containing the phosphoglycerokinase (PGK) gene promoter was used for expression of the cDNA copies of cellulase genes in yeast (23).

Enzymes. Restriction enzymes were purchased from Amersham (UK), Boehringer Mannheim (FDR) and Bethesda Research Laboratories (Gaithersburg, Md.) and used according to the manufacturers' instructions. T4 ligase and the DNA polymerase I large subunit were from Biolabs and the calf intestine phosphatase from Boehringer Mannheim. Reverse transcriptase was from Dr. J. W. Beard (Life Sciences Inc., St. Petersburg, Fla.). Protoplasting enzyme, Zymolyase 60000 was obtained from Kirin Brewery Co., Japan. Klenow fragment of *E. coli* polymerase I was from Boehringer Mannheim.

General growth media. *E. coli* HB101 was grown in L-broth. Transformants were selected on L-plates supplemented with 1.5% agar and containing 100 µg/ml ampicillin. The concentration of tetracycline added to L-plates was 10 µg/ml. Complete medium YPG for growth of yeast contained 1% yeast extract, 2% peptone, and 2% glucose. Yeast minimal medium, YMB, contained 0.67% yeast nitrogen base (Difco, Detroit, USA) and 2% sugar (lactose, cellobiose, starch or glucose). The final concentration of amino acids added was as described (24). The solidifying agent on yeast plates was 2% agar (Difco Bacto Agar). In yeast protoplast plating medium 1.2M sorbitol was added as an osmotic stabilizer. The top agar used in plating the yeast protoplasts for regeneration was prepared as minimal medium but using 3% purified agar (Difco) as a solidifying agent.

All methods unless otherwise specified are as described in Maniatis et al. 1982 (25).

Isolation and characterization of the cellulolytic genes from the fungus *T. reesei*

Polyadenylated (polyA+) messenger RNA isolated from *T. reesei* mycelia actively producing cellulases directs in the in vitro synthesis—in a rabbit reticulocyte lysate—of a number of large polypeptides that are precipitated by antibody prepared against purified cellulolytic enzymes. Messenger RNA isolated from repressed glucose grown mycelia does not direct the synthesis of these cellulase-specific polypeptides. This difference between induced and repressed populations was used to identify a collection of hybrid phages containing *T. reesei* genes strongly expressed during production of cellulolytic enzymes.

For the isolation of cellulase-specific, induced mRNAs *T. reesei* (strain VTT-D-80133) was grown as described by Bailey and Nevalainen (26) except that the medium contained 2% lactose and 2% of a soluble extract of distillers spent grain. Samples taken during cultivation were assayed for activity against dyed Avicel, hydroxyethylcellulose (HEC) and for soluble protein (26). Estimation of reducing sugars was by the method of Sumner (27).

Cellular RNA from mycelia was isolated by a modification of the method of Ohi and Short (28). The frozen mycelia was ground to a fine powder under liquid nitrogen and suspended in a buffer containing 20 mM Tris-HCl (pH 7.6), 0.1M NH4 1 mM Mg (OAc)2, 10 mM Na-iodoacetate, 0.5 mg/ml polyvinylsulfate and 2% Na-dodecyl sulfate (SDS). Following incubation at 37° C. for 30 minutes, insoluble material was removed by centrifugation at 13000 g for 10 minutes.

The poly(A)+ fraction was purified by chromatography through an oligo(dT) cellulose column (Bethesda Research Laboratories (29) and in vitro translation was carried out with a rabbit reticulocyte lysate using $^{35}$S-methionine (Amersham International Ltd) (30). Immunoprecipitation was carried out according to Dobberstein (31) using antiserum prepared against purified CBH I, CBH II or ENDO II (now EG I), or with the corresponding preimmune serum.

Table 1 shows the molecular weights of proteins precipitated by antiserum against specific cellulases analysed on 7.5–15% SDS polyacrylamide gels (32).

TABLE 1

| Antiserum | In vivo | In vitro |
| --- | --- | --- |
| CBH I | 71 000 | 67 000 |
| CBH II | 63 000 | 48 000 |
| ENDO II (now EGI) | 62 000 | 53 000 |

The construction of the *T. reesei* gene bank was carried out as follows.

Conidia of *Trichoderma reesei* were germinated in a liquid medium containing 1.5% $KH_2PO_4$, 0.5% $(NH_4)_2SO_4$, 0.06% $MgSO_4 \cdot 7H_2O$, 0.06% $CaCl_2$, 0.15% proteose peptone, 0.03% urea, 2% sucrose and minimal salts. Cultures were incubated with shaking at 29° C. for about 12 h. The isolation of nuclei was carried out using a slightly modified method of Hautala et al. (33). DNA was isolated from a crude nuclear pellet obtained by differential centrifugation of homogenized mycelium. The crude nuclear pellet was treated with SDS-amylase solution (100 mM EDTA pH 8.0, 140 mM NaCl, 1% Nadecylsulfate and 3.3% α-amylase obtained from Merck, Darmstadt, FRG) for 1 h at 37° C. Proteinase K (final concentration 0.8% w/v) was then added and incubation was continued for 2 h at 37° C. with gentle shaking. After incubation, cell debris was removed by centrifugation and DNA was precipitated from the supernatant with ethanol. The DNA was then purified by CsCl centrifugation. The chromosomal DNA from *T. reesei* was partially digested with MboI and sized by sucrose density gradient centrifugation. Fifteen-20 kb fragments were ligated to Bam HI-cleaved λ1050 DNA. In vitro packaging of the recombinant molecules was carried out using packaging extracts prepared by the method of Hohn as described by Maniatis et al. (25).

Recombinant phages were transferred from the agar to nitrocellulose filters (Schleicher & Schüll, BA 85) as described by Benton and Davis (34). cDNAs made from induced mRNA (described earlier) and from mRNA isolated from fungus grown in the presence of glucose were used as probes. cDNA first strand synthesis was carried out by the procedure of Efstradiatis et al. (35) but using 10 μCi of 32 pαATP per 50 μl reaction. The in situ plaque hybridization was carried out according to Maniatis et al. (25). Hybridization was detected by autoradiography of the filters on Kodak X-OMAT film. Positive plaques were picked into 1 ml of SM (25) and a drop of chloroform and stored at −4° C.

Hybrid phage hybridizing only to cDNA made with induced mRNA containing cellulase coding sequences were purified extensively and retested by hybridization to both probes. A number of different hybrid clones that hybridized strongly to the induced cellulase probe were identified and selected for further analysis.

The hybrid phages containing genes induced when the fungus produces cellulases were first grouped according to their restriction enzyme patterns. Then the particular cellulase gene in each group was identified by hybrid selection of messenger RNA.

DBM paper was obtained from Schleicher and Schüll (Keene, N. H.) and activated according to the maker's instructions. Binding of DNA to the activated paper and RNA hybridization and elution was carried out according to Maniatis et al. (25). RNA was translated with a rabbit reticulocyte lysate supplied by Amersham International Ltd. and the proteins produced were labeled with $^{35}S$-methionine. The proteins were analysed by autoradiography on Kodak X-OMAT film after separation on a 7-15% polyacrylamide gradient denaturing gel.

The size of the proteins obtained from particular phage by hybrid selection and their cross reaction with specific antiserum is shown in Table 2.

TABLE 2

| Hybrid Phage No. | 44A | W17A | W12A |
|---|---|---|---|
| Mol. weight of major protein produced from hybrid selected message | 67 000 | 48 000 | 53 000 |
| Cross reaction of major protein with antisera against | | | |
| CBH I | + | − | − |
| CBH II | − | + | − |
| ENDO II (now EGI) | − | − | + |

Single and double digests of the clone 44A, were analyzed on 0.6% and 1.5% agarose gels. The fragments were electrophoretically transferred to Gene Screen membranes (New England Nuclear, Massachusetts) and hybridized to the induced cDNA probe as instructed by the manufacturer.

This procedure permitted the construction of restriction enzyme maps of three cellulose genes. These restrictions enzyme maps are shown in FIGS. 1, 2 and 3.

The nucleotide sequence of the CBH I, CBH II and ENDO II (now EG I) genes was generated by dideoxy sequencing (36) using restriction enzyme fragments or DNA fragments obtained by the "shotgun" procedure (37).

The construction of a yeast vector containing the CBH I chromosomal gene

The hybrid phage 44A (11) DNA containing the CBH I of *Trichoderma reesei* hypercellulolytic mutant strain VTT-D-80133, was digested with Pst I to give a mixture of fragments one of which being about 12 kb and containing the entire CBH I gene with its own regulatory sequences. The resulting DNA-fragments were ligated with the yeast cosmid p3030 digested partially with the same enzyme.

The yeast strain OL1 was transformed to his+ with the DNA-mixture described above. Transformation was carried out essentially as described by Gerbaud et al. (38). Transformed cells were plated on yeast minimal medium with leucine and uracil but lacking histidine.

The clones were further tested in situ plaque hybridization for the presence of the CBH I gene originated from *T. reesei*.

The presence of an intact CBH I gene in yeast was ensured by isolating total DNA (39) from a transformant colony and digesting it with restriction enzymes Bgl II and Hinc II. DNA was transferred to nitrocellulose filter (40) from agarose gel and hybridized to a M13 probe (41) containing the 0.7 kb Eco RI fragment from CBH I gene. FIG. 4 shows the construction of a hybrid plasmid containing the CBH I gene.

Isolation of full length cDNAs coding for the enzymes CBH I, CBH II and ENDO II (now EG I)

A cDNA bank from *T. reesei* was made from induced mRNA isolated from cells as described earlier. However, after the frozen mycelia had been ground under liquid nitrogen it was suspended in 5 volumes a guanidinium isothiocyanate buffer as described by Maniatis et al. (25). The RNA preparation was then carried out as described (42). cDNA first strand synthesis was carried out according to Maniatis (25) and the second strand was carried out according to Gubler and Hoffmann (43). The double stranded cDNA was then treated with $T_4$-polymerase to give blunt ends and small cDNAs less than 500 nucleotides long removed by passage through a CL-4B column (Pharmacia). Long cDNAs were then ligated to a Sma I digested and phosphatase treated preparation of pUC 8 vector. The ligation mixture was used to transform E. coli strain JM 105 and the cDNA bank was stored on nitrocellulose filters.

Full length cDNAs coding for CBH I, CBH II and ENDO II (now EG I) were isolated from a cDNA bank using specific restriction fragments as probes. For the identification of CBH I, a radioactive Eco RI-Hind III fragment from the 5' end of the chromosomal gene was used to identify long cDNAs. A plasmid pTT01 from a clone containing sequences homologous to this Eco RI-Hind III fragment was further characterized by sequencing of the cDNA ends by double stranded dideoxy sequencing. 1 μg of purified plasmid was denatured in 0.4M NaOH at room temperature for 5 minutes at a concentration of 100 ng/μl. 5 μl of sequencing or reverse sequencing primer (Amersham) was added and the mixture was precipitated with ethanol. After washing the pellet was resuspended in 10 μl at 14 mM Tris pH 8–7 mM MgCl$_2$. Sequencing reactions were done according to general methods (36) except that temperature was kept at 37° C. CBH II cDNAs were isolated using a Pvu II fragment from the 5' end of the chromosomal gene and the plasmid pTT09 characterized as for the CBH I cDNA. ENDO II (now EG I) cDNAs were identified using a Kpn I-Sal I fragment from the 5' end of the gene and plasmid pTT11 also characterized as for the CBH I cDNA. Plasmid pTT11 is shown on FIG. 9. A transformed E. coli host (ALKO2296) carrying plasmid pTT11 (called pTTc11) was deposited at the DSM-Deutsche Sammlung von Mikroorganismen und Zellkulturen Gmbh, Mascheroder Weg 1B, D-3300 Braunschweig, Germany, on Jan. 15, 1992 as deposit number DSM6873. All cDNAs were then sequenced to determine that their sequence corresponded to that of the gene from which they are transcribed. The DNA sequences of CBH II and ENDO II (now EG I) cDNAs are shown in FIGS. 5 and 6. The cDNA sequence of CBH I was identical to that already described (10).

The construction of expression vectors containing cDNAs for the production of fungal cellulases in yeast The efficient yeast expression vector pMA 91 has been assembled using the regulatory sequences of the yeast phosphoglycerokinase (PGK) gene (23). The sequences coding for the amino acid sequence of the enzyme have been removed from the gene and replaced by a single Bgl II site. This deleted gene has then been inserted into a yeast/coli shuttle plasmid.

a) CBH I expression vector (FIG. 7)

The CBH I cDNA was removed from plasmid (pTT01 FIG. 7) by digestion with Hinc II and the cDNA fragment isolated from an agarose gel.

pMA 91, the expression vector was cleaved with Bgl II and the ends were filled in with the Klenow fragment. The vector was treated with phosphatase, ligated to the cDNA and transformed into E. coli strain HB101 by selection for expression of the vector leucine gene (FIG. 7). Plasmid DNA was isolated from a number of transformants and those clones containing the cDNA insert in the correct orientation with respect to the PGK promotor—as identified by restriction enzyme analysis—were retained. DNA from one of these clones (pMP 11) was then transformed into yeast strain MT 302-1c by the method described earlier by selection of the leucine marker of pMA 91 resulting in strain VTT-RC-84011.

b) CBH II expression vector (FIG. 8).

CBH II cDNA was removed from plasmid pTT 09 using Eco RI and Bam HI. The ends of the DNA were filled in with Klenow fragment. The cDNA fragment was then isolated from an agarose gel and ligated to the vector pMA 91 prepared as for CBH I.

The ligation mix was transferred into HB101 and clones containing the cDNA in the correct orientation identified. FIG. 8 shows the DNA sequence at the junctions between pMA 91 and the cDNA.

Figure 9B:
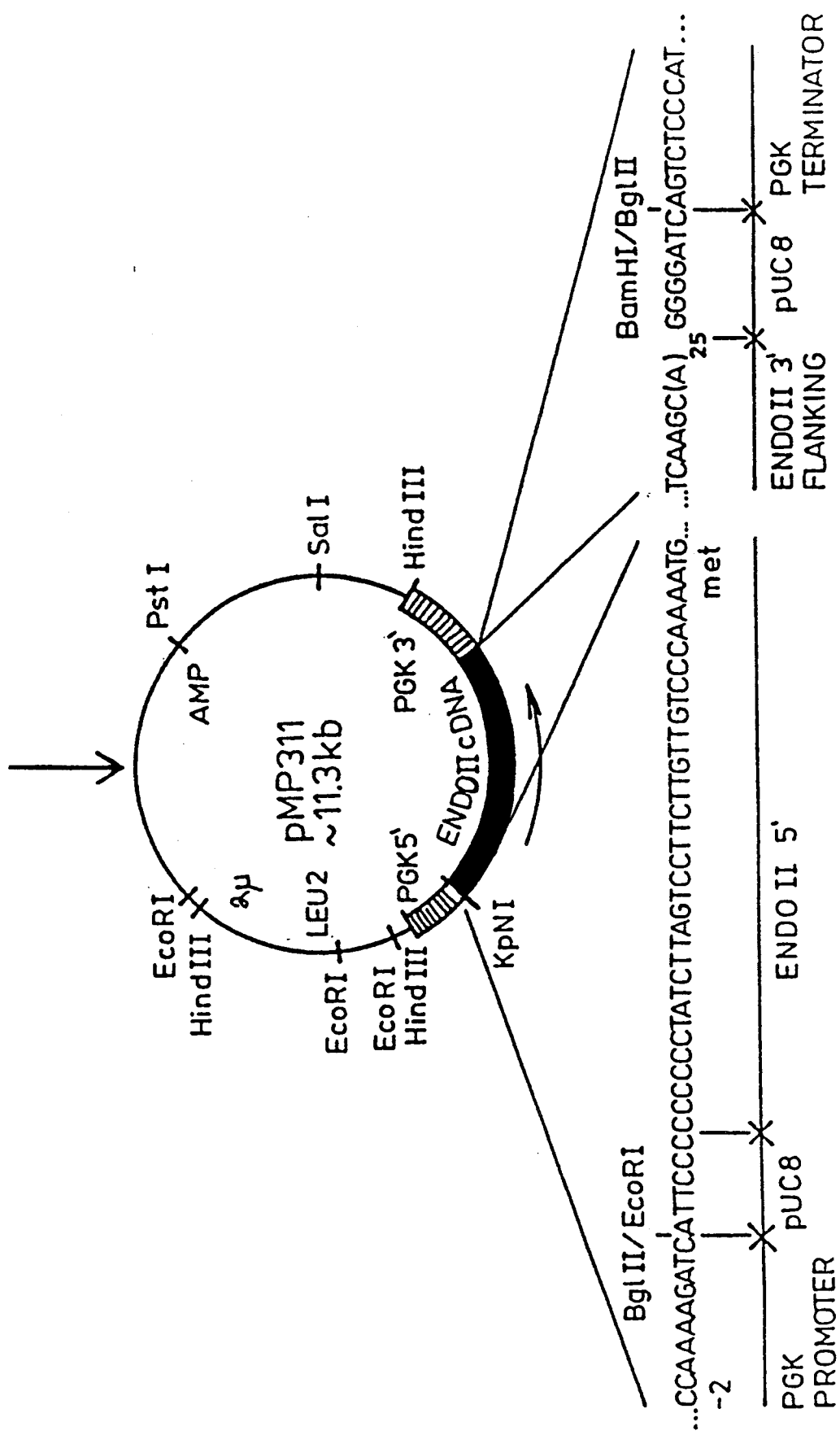

Plasmid pMP 29 with the cDNA in the correct orientation was then used to transform yeast MT302-1c by selection for the leucine marker to give strain VTT-RC-84012.

c) ENDO II (Now EGI) expression vector (FIG. 9)

The ENDO II (Now EGI) cDNA was transferred to pMA 91 exactly in the sam way as CBH II cDNA. FIG. 9 shows the DNA sequences at the junctions between pMA 91 and the ENDO II (Now EGI) cDNA. The plasmid, pMP 311 containing the ENDO II (Now EGI) cDNA in the correct orientation was transferred to yeast as described earlier to give strain VTT-RC-84013.

Culturing the hybrid yeast strains to produce the cellulolytic enzymes, CBH I, CBH II and ENDO II (Now EGI)

Strain VTT-RC-84001 containing YEpNPO3 was grown in a yeast minimal medium with leucine and uracil for three days after which complete medium (⅓ volume) was then added to allow the cells to pass through one more division.

Strains VTT-RC-84011 (CBH I cDNA), VTT-RC-84012 (CBH II cDNA) and VTT-RC-84013 (ENDO II (Now EGI) cDNA) were grown in a yeast minimal medium containing arginine, histidine and adenine for three days after which complete medium ⅓ volume was added to allow the cells to pass through one more division. The final volume of the cultures was about 150 ml.

Preparation of different fractions for analysis of the location of enzyme activity Three fractions were prepared from hybrid yeast cultures for analysis of enzyme activity. Fraction 1 comprised the growth medium without the cells. Fraction 2 comprises the supernatant left when protoplasts are pelleted and fraction 3 comprises the supernatant of lysed protoplasts.

After cultivation yeast cells were collected by centrifugation and the supernatant was saved (Fraction 1). The resulting pellet was washed twice with distilled water and 1.2M sorbitol. The pellet was then resuspended in protoplasting buffer (1.2M sorbitol, 10 mM Tris and 10 mM CaCl, pH 7.6) and Zymolyase 60000 was added at a concentration of 30 μg/ml of protoplasting suspension. Suspension was incubated in a waterbath at 37° C. for 60 minutes with gentle shaking. The protoplasts so formed were pelleted and the resulting supernatant (periplasmic cell contents) (Fraction 2) saved for enzyme activity determinations. In some cases fractions 1 and 2 were concentrated by ultrafiltration (Amicon). Protoplast pellets were washed with cold 1.2M sorbitol and resuspended in 1.2 ml of 5 mM citrate buffer pH 5.0, pelleted and the supernatant was saved (Fraction 3).

Measurement of cellulase enzyme activity produced by the hybrid yeasts

1 CBH I activity from VTT-RC-84001

The three different fractions were tested for CBH I enzyme activity using amorphous ball milled cellulose which is attached only by cellobiohydrolases (44). The total protein concentration of the samples was about 300 μg/ml. Hydrolysis of the substrate caused by active cellobiohydrolase enzyme was measured by following the change in absorbance at 620 nm. CBH I type activity was found only in fraction 2, the periplasmic or intramural space.

FIG. 10 shows the activity of the CBH I enzyme produced by the yeast strain VTT-RC-84001 and secreted into the intramural space as compared to the control yeast containing only vector p3030 DNA and 1 μg of Trichoderma CBH I. This Figure shows that the hybrid yeast strain produces active CBH I, which appears to be at least as resistant to incubation at 50° C. for 3 days as in the native enzyme. The CBH I produced by the yeast represents 1-2% of the protein of intramural space protein.

As the intron sequences of fungus are different from those of yeast it is not likely that yeast would process off the fungus gene introns. Probably for that reason the product of the chromosomal gene remains in the yeast periplasmic space and is not secreted from the cell as is the product coded by the cDNA sequence. This result suggests that transferring the chromosomal gene coding for CBH I to yeast, results in the production of a smaller protein, which, however, has the same type of activity as the full length cellulase.

2 CBH I activity from VTT-RC-84011

The three different fractions were tested for CBH I enzyme activity as just described. However, in this case, most of the CBH I type activity was found in the growth medium. The results, with a final protein concentration during hydrolysis of 5 μg/ml is very similar to that shown in FIG. 10. The CBH I enzyme produced with this construction represented 1-5% of total cell protein.

3 CBH II activity from VTT-RC-84012

The three different fractions were tested from cellobiohydrolase activity as described for strain VTT-RC-84001. As with strain VTT-RC-84011, most of the cellobiohydrolase type activity was found in the growth medium. The results with a final protein concentration of 10 μg/ml is similar to that shown in FIG. 10. The CBH II enzyme produced with this construction represented 1-5% of total cell protein.

4 ENDO II (Now EGI) activity from VTT-RC-84013

The three different fractions were tested for endoglucanase activity by following the hydrolysis of 0.1% β-glucan at 50° C.

The reducing sugars liberated in 5 minutes (overnight) were measured as glucose using the dinitro salisylic acid method (45). Most of the ENDO II (Now EGI) activity was found secreted into the growth medium. The ENDO II (Now EGI) enzyme produced with this construction represented 1-5% of total cell protein.

It is considered that the invention and many of its attendant advantages will be understood from the foregoing description and that it will be apparent that various changes may be made in the steps of the described method for mature protein synthesis without departing from the spirit and scope of the invention or sacrificing all of its material advantages, the method herein before described being merely a preferred embodiment.

REFERENCES

1. B. S. Montenecourt, 1983, Technol. in Biotechnology 1, 156-161.
2. ENARI, T-M. Microbiol. Cellulases, p. 183-223. In: Microbiol. Enzymes and Biotechnologes. William M. Fogart (ed.). Applied Science Publishers, London and New York.
3. Shoemaker, S. P. and Brown, R. D. Jr. (1978a) Biochim. Biophys. Acta 523, 133-146.
4. Shoemaker, S. P. and Brown, R. D. Jr. (1978b) Biochim. Biophys. Acta 523, 147-161.
5. Fägerstam, L. and Petterson, L. G. (1979) FEBS Lett. 98, 363-367.
6. Fägerstam, L. and Petterson, L. G. (1980) FEBS Lett. 119 97-100.
7. Sprey, B. and Lambert, C. (1983) FEMS Microbiol. Lett. 18, 217-222.
8. Chanzy, H., Henrissat, B., Vuong, R. and Schulein, M. (1983) FEBS Lett. 153, 113-118.
9. Nummi, M., Niku-Paavola, M. L., Lappalainen, A., Enari, T. M. and Raunio, V. (1983) Biochem. J. 215, 677-683.
10. Shoemaker, S., Schweickart, V., Ladner, M. Gelfand, D., Kwok, S., Myambo, K. and Innis, M. (1983) Biotechnol. 1. 691-696.
11. Teeri, T., Salovuori, I. and Knowles J. (1983), Biotechnol. 1, 696-699.
12. Penttilä, M. E., Nevalainen, K. M. H., Raynal, A. and Knowles, J. C. K. 1984: Molec., Gen. Genetics 194:494-499)
13. Hitzeman, R. A., F. E. Hagie, H. L. Levine, D. V. Goeddel, G Ammerer & B. D. Hall: Expression of a human gene for interferon in yeast. Nature 293, 717-722 (1981).
14. Valenzuela, P., A. Medina, W. J. Rutter, G. Ammerer & B. D. Hall: Synthesis and assembly of hepatitis B virus surface antigen particles in yeast. Nature 298, 347-350 (1982).
15. Mellor, J., M. J. Dobson, M. A. Roberts, M. F. Tuite, J. S. Emtage, S. White, P. A. Lowe, T. Patel, A. J. Kingsman & S. M. Kingsman: Efficient synthesis of enzymatically active calf chymosin in Saccharomyces cerevisiae. Gene 24 (1983): 1-14.
16. K. K. Thomsen, 1983, Carlsberg Res. Commun. 48 p. 545-555.
17. Mandels, M., Weber, J. and Parrek, R. (1971) Appl. Microbiol. 21, 152-154.
18. Nevalainen K. M. H. 1981: Appl. Environ. Microbiol. 41: 595-596.
19. Karn, J., Brenner, S., Barnett, L., and Cesaveni, G. 1980. Novel bacteriophage cloning vector. Proc. Natl. Acad. Sci. 77:5172-5176.
20. Messing, J., Crea, R., and Seeburg, P. H. 1981. A system for shotgun DNA sequencing. Nucleic Acids Res. 9: 309-321.
21. Vieira, J. and Messing, J. 1982: Gene 19:259-268.
22. Boy-Marcotte, E., Jaquet, M, (1982) A dictyostelium discoideum DNA fragment complements a Saccharomyces cerevisiae ura3 mutant. Gene 20:433-440.
23. Mellor, J., Dobson, M. J., Roberts, N. A., Tuite, M. F., Emtage, J. S., White, S., Lowe, P. A., Patel, T., Kingsman, A. J. and Kingsman, S. M. 1983. Efficient synthesis of enzymatically active calf chymosin in Saccharomyces cerevisiae. Gene 24: 1-14.
24. Sherman, F., Fink, G. R. and Hicks, J. B. 1981. Methods in yeast genetics. Cold Spring Harbor Laboratory, New York. p. 62.
25. Maniatis, T., Fritsch, E. F. and Sambrook, J. 1982. Molecular cloning: A laboratory manual. Cold Spring Harbor Laboratory, Cold Spring Harbor, N.Y.
26. Bailey, M. J. and Nevalainen, K. M. H. 1981. Induction, isolation and testing of stable Trichoderma reesei mutants with improved production of solubilizing cellulase. Enzyme Microb. Technol. 3:153–157.
27. Sumner, J. B. and Somers, G. F. (1949) in Laboratory experiments in biological chemistry 2nd ed. pp. 38–39, Academic Press, New York.
28. Ohi, S., and Short, J. 1980. A general procedure for preparing messenger RNA from eukaryotic cells without using phenol. J. Appl. Microbiol. 2:398–413.
29. Aviv, H. and Leder, P. (1972) Proc. Natl. Acad. Sci. 69 1408–1412.
30. Pelham, H. R. B. and Jackson, R. J. (1976) Env. J. Biochem. 67 pp. 247–256.
31. Dobberstein, B., Garoff, H. and Wawen, G. (1979) Cell 17, 759–769.
32. Laemmli, U. 1970. Cleavage of structural proteins during the assembly of bacteriophage T4. Nature 227: 680–685.
33. Hautala, J. A., Corner, B. H., Jacobson, J. W., Patel, G. L. and Giles, N. H. 1977. Isolation and characterization of nuclei from Neurospova crassa. J. Bacterial. 130: 704–713.
34. Benton, W. D. and Davis, R. W. 1977. Screening$\lambda_{gt}$ recombinant clones by hybridization to single plaques in situ. Science 196:180–182.
35. Efstradiatis, A., Kafatos, F. C., Maxam, A. M. and Maniatis, T. 1976. Enzymatic in vitro synthesis of globi genes. Cell 7:279–288.
36. Sanger, F., Nicklen, S. and Coulson, A. R. 1977. Proc. Natl. Acad. Sci. USA 74:5463–5467.
37. Deiniger, P. L. 1983: Anal. Biochem. 129: 216–223.
38. Gerbaud, C., Faurnier, P., Blanc, H., Aigle, M., Heslot, H. and Guerinau, M. 1979. Gene 5:233–253.
39. Sherman F. Fink, G. R. and Hicks, J. B. 1981: Methods in yeast genetics. Cold Spring Harbor Laboratory, New York, pp. 77–80.
40. Southern, E. M. 1975. J. Mol. Biol. 98: 503–517.
41. Hu, N. and Messing, S. 1982. Gene 17:271–277.
42. Chirgwin, J. M., Przybyla, A. E., MacDonald, R. J. and Rutter, W. J. 1979. Isolation of biologically active ribonucleic acid from sources enriched in ribonuclease. Biochemistry 18: 5294–5299.
43. Gubler and Hoffman 1983: Gene 25:263
44. Nummi, M., Fox, P. C., Niku-Paavola, M. L., and Enari, T-M 1981 Anal. Biochem. 116:133–136.
45. Kirsop, B. H. 1953: J. Inst. Brewing 59:378.

What is claimed is:

1. A substantially pure DNA molecule comprising DNA encoding a polypeptide comprising the mature endoglucanase I protein amino acid sequence shown in FIG. 6 or FIG. 11.

2. The DNA molecule of claim 1, additionally comprising DNA encoding the endoglucanase I signal sequence, said DNA encoding said signal sequence being operably linked to said DNA encoding said polypeptide, said DNA for said signal sequence having the DNA sequence encoding the peptide MetAlaProSerValThrLeuProLeuThr-
ThrAlaIleLeuAlaIleAlaArgLeuValAlaAla.

3. The DNA molecule of claim 2, wherein said DNA encoding said endoglucanase I signal sequence has the DNA sequence

ATGGCGCCCTCAGTTACACTGCCGTTGAC-
CACGGCCATCCTGG-
CNATTGCCCGGCTCGTCGCCGCC.

4. A substantially pure DNA molecule comprising the cDNA sequence shown in FIG. 6 or FIG. 11, encoding a polypeptide comprising the mature endoglucanase I protein amino acid sequence shown in FIG. 6 or FIG. 11.

5. The DNA molecule of claim 4, additionally comprising DNA encoding the endoglucanase I signal sequence, said DNA encoding said signal sequence being operably linked to said DNA encoding said polypeptide, said DNA for said signal sequence having the DNA sequence encoding the peptide MetAlaProSerValThrLeuProLeuThr-
ThrAlaIleLeuAlaIleAlaArgLeuValAlaAla.

6. The DNA molecule of claim 5, wherein said DNA encoding said endoglucanase I signal sequence has the DNA sequence

ATGGCGCCCTCAGTTACACTGCCGTTGAC-
CACGGCCATCCTGG-
CNATTGCCCGGCTCGTCGCCGCC.

7. A substantially pure DNA molecule encoding an amino acid sequence comprising the endoglucanase I signal sequence shown in FIG. 6 or FIG. 11, said endoglucanase I signal DNA sequence encoding the peptide MetAlaProSerValThrLeuProLeuThr-
ThrAlaIleLeuAlaIleAlaArgLeuValAlaAla.

8. The substantially pure DNA molecule of claim 7, wherein said DNA sequence encoding signal DNA sequence has the DNA sequence

ATGGCGCCCTCAGTTACACTGCCGTTGAC-
CACGGCCATCCTGG-
CNATTGCCCGGCTCGTCGCCGCC.

9. A recombinant DNA vector comprising the DNA sequence of any of claims 1, 3, 4, 6, 8, 2, 5, or 7.

10. A host cell transformed with the vector of claim 9.

11. The host cell of claim 10 wherein said host cell is E. coli.

12. The host cell of claim 10 wherein said host is a yeast host.

13. The yeast host cell of claim 12, wherein said host is of the genus Saccharomyces.

14. The yeast host cell of claim 13, wherein said Saccharomyces host is S. cerevisiae.

15. Plasmid pTT11.

16. E. coli host ALKO2296 having deposit number DSM6873.

* * * * *

UNITED STATES PATENT AND TRADEMARK OFFICE
CERTIFICATE OF CORRECTION

PATENT NO. : 5,393,670

Page 1 of 3

DATED : February 28, 1995

INVENTOR(S): KOWLES et al.

It is certified that an error appears in the above-identified patent and that said Letters Patent is hereby corrected as shown below.

Replacement Figure 6A-6B

And replace therein with the figure on page 2 & 3.

UNITED STATES PATENT AND TRADEMARK OFFICE
CERTIFICATE OF CORRECTION

PATENT NO. : 5,393,670

DATED : February 28, 1995

INVENTOR(S) : KOWLES et al.

It is certified that error appears in the above-indentified patent and that said Letters Patent is hereby corrected as shown below:

Delete Figure 6A-6B:

FIG.6A

UNITED STATES PATENT AND TRADEMARK OFFICE
CERTIFICATE OF CORRECTION

PATENT NO. : 5,393,670

DATED : February 28, 1995

INVENTOR(S) : KOWLES et al.

Page 3 of 3

It is certified that error appears in the above-indentified patent and that said Letters Patent is hereby corrected as shown below:

FIG.6B

Signed and Sealed this

Second Day of September, 1997

Attest:

*Attesting Officer*

BRUCE LEHMAN

*Commissioner of Patents and Trademarks*

UNITED STATES PATENT AND TRADEMARK OFFICE
CERTIFICATE OF CORRECTION

PATENT NO. : 5,393,670  
DATED : February 28, 1995  
INVENTOR(S) : Jonathan Knowles, et. al.

Page 1 of 3

It is certified that error appears in the above-identified patent and that said Letters Patent is hereby corrected as shown below:

Drawings:

The correction to FIG. 6A, in the Certificate of Correction issued September 2, 1997, should be corrected as shown on the attached page.

Signed and Sealed this

Twenty-fifth Day of July, 2000

Attest:

Q. TODD DICKINSON

*Attesting Officer*  *Director of Patents and Trademarks*

UNITED STATES PATENT AND TRADEMARK OFFICE
CERTIFICATE OF CORRECTION

PATENT NO. : 5,393,670

DATED : February 28, 1995

INVENTORS : Knowles et al.

It is certified that an error appears in the above-identified patent and that said Letters Patent is hereby corrected as shown below.

Delete Figure 6A:

And replace therein with the figure on page 2 of 2.

FIG.6A

UNITED STATES PATENT AND TRADEMARK OFFICE
CERTIFICATE OF CORRECTION

PATENT NO. : 5,393,670

DATED : February 28, 1995

INVENTORS : Knowles et al.

It is certified that an error appears in the above-identified patent and that said Letters Patent is hereby corrected as shown below.

Replacement Figure 6A:

```
                                              pUC8
                                    CCCCCCTATCTTACTCCTTCTTCTTCTCCCAAA
        ┌─────ENDO II signal  sequence─────────┐  Kpn I
ATGCCCCCCTCAGTTACACTGCCCGTTGACCACCCCCATCCTCCCAATTCCCCCCCTCCTCCCCCCCACCAACCCCGTACCAGCCACCCCC
MetAlaProSerValThrLeuProLeuThrThrAlaIleLeuAlaIleAlaArgLeuValAlaAlaGlnGlnProGlyThrSerThrPro    30

GAGGTCCATCCCAAGTTGACAACCTACAAGTGTACAAAGTCCCCCCCGTGCCTGCCCCACGACACCTCCGTCCTCCTTGACTGGAACTAC
GluValHisProLysLeuThrThrTyrLysCysThrLysSerGlyCysValAlaGlnAspThrSerValValLeuAspTrpAsnTyr     60

CCCTCGATGCACCACCCCAAACTACAACCTCGTCCACCGTCAACCCCCCCGGTCAACACCACCTCTGCCCTGACGACCCCGACCTGTGCCAAG
ArgTrpMetHisAspAlaAsnTyrAsnSerCysThrValAsnGlyCysValAsnThrLeuCysProAspGluAlaThrCysGlyLys    90

Sal I
AACTGCTTCATCGAGGGCGTCGACTACCCCGCCTCCGGGCGTCACCACCTCCCCCAGCACCCTCACCATGAACCAGTACATGCCCAGCAGC
AsnCysPheIleGluGlyValAspTyrAlaAlaSerGlyValThrThrSerGlySerSerLeuThrMetAsnGlnTyrMetProSerSer  120

TCTGGCGCCTACAGCAGCGTCTCTCCTCGCCTGTATCTCCTGGACTCTGACCGTGACTACCTGATCCTGAACCTCAACCCCCACGACCTG
SerGlyGlyTyrSerSerValSerProArgLeuTyrLeuLeuAspSerAspValGlyTyrValMetLeuLysLeuAsnGlyGlnGluLeu  150

Sal I
AGCTTCGACGTCGACCTCTCTGCTCTGCCCGTCTGCACACAACCCCTCCCTCTACCTGTCTCAGATGGACGACAACCCCGGCGCCAACCAG
SerPheAspValAspLeuSerAlaLeuProCysGlyGluAsnGlySerLeuTyrLeuSerGlnMetAspGluAsnGlyAlaAsnGln   180

TATAACACGGCCGGGTGCCAACTACCCGGAGCGGCTACTCCGATCCTCAGTGCCCCGTCCAGACATGGACGAACCGCCACCCTCAACACTACC
TyrAsnThrAlaGlyAlaAsnTyrGlySerGlyTyrCysAspAlaGlnThrTrpArgAsnGlyThrLeuAsnThrSer           210

Xho I
CACCACCGGCTTCTGCTCCAACCACATGGATATCCTGCAGCCCAACTCCAGCCCGAATGCCTTGACCCCTCACTCTTGCACCGCCACCGCC
HisGlnGlyPheCysCysAsnGluMetAspIleLeuGlyAsnSerArgAlaAsnAlaLeuThrProHisSerCysThrAlaThrAla    240

TGCGACTCTGCCGGTTGCGCCTTCAACCCCTATCCCACCCCCTACAAAACCTACTACCCCCCCCGAGATACCGTTGACACCTCCAACACC
CysAspSerAlaGlyCysGlyPheAsnProTyrGlySerGlyTyrLysSerTyrTyrGlyProGlyAspThrValAspThrSerLysThr  270
                                                                              Sal I
TTCACCATCATCACCCAGTTCAACACGGACAACGCCTCCCCCTCGGGCAACCTTGTCAGCATCACCCGCAAGTACCAGTCCCCCCGTCGAC
PheThrIleIleThrGlnPheAsnThrAspAsnGlySerProSerGlyAsnLeuValSerIleThrArgLysTyrGln......ValAsp  300

ATCCCCACCCCCCAGCCCCCCCGCGACACCATCTCGTCCTGCCCGTCCCCCTCAGCCTACCCCGCCTCGCCACCATGGGCAAGCCCCTG
IleProSerAlaGlnProGlyGlyAspThrIleSerSerCysProSerAlaSerAlaTyrGlyLeuAlaThrMetGlyLysAlaLeu    330
                                                                                    Pst I
AGCAGCGGCATCGTGCTCGTGTCTTCACCCATTTGGAACGACAACACCCAGTACATGAACTGCCTCGACAGCCCCAACCCCCCCCCCTGCACC
SerSerGlyMetValLeuValPheSerIleTrpAsnAspAsnSerGlnTyrMetAsnTrpLeuAspSerGlyAsnAlaGlyProCysSer  360
```

FIG.6A